(12) United States Patent
Stopek et al.

(10) Patent No.: US 9,364,215 B2
(45) Date of Patent: * Jun. 14, 2016

(54) MEDICAL DEVICE PACKAGE

(75) Inventors: Joshua Stopek, Wallingford, CT (US);
Joseph Hotter, Middletown, CT (US);
Matthew D. Cohen, Berlin, CT (US)

(73) Assignee: Covidien LP, Mansfield, MA (US)

( * ) Notice: Subject to any disclaimer, the term of this patent is extended or adjusted under 35 U.S.C. 154(b) by 1014 days.

This patent is subject to a terminal disclaimer.

(21) Appl. No.: 11/954,426

(22) Filed: Dec. 12, 2007

(65) Prior Publication Data

US 2008/0128296 A1    Jun. 5, 2008

Related U.S. Application Data

(63) Continuation-in-part of application No. 11/340,912, filed on Jan. 26, 2006, now abandoned.

(51) Int. Cl.
*A61B 17/06* (2006.01)
*A61B 19/02* (2006.01)
*A61B 17/00* (2006.01)

(52) U.S. Cl.
CPC ......... *A61B 17/06114* (2013.01); *A61B 19/026* (2013.01); *A61B 17/06166* (2013.01); *A61B 2017/00893* (2013.01); *A61B 2019/0219* (2013.01); *A61B 2019/0267* (2013.01); *A61B 2019/0268* (2013.01); *A61B 2019/0274* (2013.01)

(58) Field of Classification Search
USPC ...................................... 206/63.3, 524.4, 438
See application file for complete search history.

(56) References Cited

U.S. PATENT DOCUMENTS

| | | | | |
|---|---|---|---|---|
| 2,197,717 | A | * | 4/1940 | Bradshaw ........................ 422/28 |
| 2,764,979 | A | | 10/1956 | Henderson |
| 3,545,608 | A | * | 12/1970 | Schneider et al. ............ 206/63.3 |
| 3,648,949 | A | * | 3/1972 | Berger et al. .................. 242/159 |
| 3,905,375 | A | | 9/1975 | Toyama |
| 4,018,222 | A | | 4/1977 | Mcaleer et al. |
| 4,113,090 | A | | 9/1978 | Carstens |
| 4,259,184 | A | | 3/1981 | D'Arnal |
| 4,366,901 | A | | 1/1983 | Short |
| 4,387,727 | A | | 6/1983 | Sandstrom |
| 4,423,819 | A | * | 1/1984 | Cummings ................... 215/232 |
| 4,424,898 | A | | 1/1984 | Thyen et al. |
| 4,699,271 | A | | 10/1987 | Lincoln et al. |
| 4,896,767 | A | | 1/1990 | Pinheiro |
| 4,961,498 | A | | 10/1990 | Kalinski et al. |

(Continued)

FOREIGN PATENT DOCUMENTS

| | | |
|---|---|---|
| DE | 43 23 666 | 1/1994 |
| EP | 0418059 | 3/1991 |

(Continued)

OTHER PUBLICATIONS

European Search Report for EP 08253979.2-2310 date of completion is Apr. 21, 2009.

(Continued)

*Primary Examiner* — Anthony Stashick
*Assistant Examiner* — Blaine Neway

(57) ABSTRACT

The present disclosure provides a package for a medical device having a surface prepared for receiving a target agent and a port for permitting the passage of the target agent between the surface of the medical device contained therein.

12 Claims, 2 Drawing Sheets

(56) References Cited

U.S. PATENT DOCUMENTS

| | | | |
|---|---|---|---|
| 4,967,902 A | 11/1990 | Sobel et al. | |
| 5,024,322 A | 6/1991 | Holzwarth | |
| 5,052,551 A | 10/1991 | Cerwin et al. | |
| 5,056,658 A | 10/1991 | Sobel et al. | |
| 5,099,994 A | 3/1992 | Kalinski et al. | |
| 5,131,533 A | 7/1992 | Alpern | |
| 5,165,217 A | 11/1992 | Sobel et al. | |
| 5,179,818 A | 1/1993 | Kalinski et al. | |
| 5,180,053 A | 1/1993 | Cascio et al. | |
| 5,192,483 A | 3/1993 | Kilgrow et al. | |
| 5,213,210 A | 5/1993 | Cascio et al. | |
| 5,222,978 A | 6/1993 | Kaplan et al. | |
| 5,228,565 A | 7/1993 | Sinn | |
| 5,230,424 A | 7/1993 | Alpern et al. | |
| 5,236,083 A | 8/1993 | Sobel et al. | |
| 5,246,104 A | 9/1993 | Brown et al. | |
| 5,249,671 A | 10/1993 | Sinn | |
| 5,249,673 A | 10/1993 | Sinn | |
| 5,263,585 A | 11/1993 | Lawhon et al. | |
| 5,271,495 A | 12/1993 | Alpern | |
| 5,284,240 A | 2/1994 | Alpern et al. | |
| 5,350,060 A | 9/1994 | Alpern et al. | |
| 5,359,831 A | 11/1994 | Brown et al. | |
| 5,366,081 A | 11/1994 | Kaplan et al. | |
| 5,392,918 A * | 2/1995 | Harrison | 206/571 |
| 5,407,071 A | 4/1995 | Lawhon et al. | |
| 5,417,036 A | 5/1995 | Brown et al. | |
| 5,433,315 A | 7/1995 | Brandau | |
| 5,447,966 A | 9/1995 | Hermes et al. | |
| 5,462,162 A | 10/1995 | Kaplan et al. | |
| 5,468,252 A | 11/1995 | Kaplan et al. | |
| 5,472,081 A | 12/1995 | Kilgrow et al. | |
| 5,489,294 A * | 2/1996 | McVenes et al. | 607/120 |
| 5,503,266 A | 4/1996 | Kalbfeld et al. | |
| 5,575,382 A | 11/1996 | Sobel et al. | |
| 5,628,395 A | 5/1997 | Daniele et al. | |
| 5,655,652 A | 8/1997 | Sobel et al. | |
| 5,669,490 A | 9/1997 | Colligan et al. | |
| 5,675,961 A | 10/1997 | Cerwin et al. | |
| 5,681,740 A * | 10/1997 | Messier et al. | 435/284.1 |
| 5,704,469 A | 1/1998 | Daniele et al. | |
| 5,733,293 A | 3/1998 | Scirica et al. | |
| 5,788,062 A | 8/1998 | Cerwin et al. | |
| 5,837,234 A * | 11/1998 | Gentile et al. | 424/93.7 |
| 5,887,706 A | 3/1999 | Pohle et al. | |
| 5,906,273 A | 5/1999 | Pohle et al. | |
| 5,918,733 A | 7/1999 | Cerwin et al. | |
| 5,954,748 A * | 9/1999 | Totakura | 606/229 |
| 5,960,956 A * | 10/1999 | Langanki et al. | 206/440 |
| 6,016,905 A | 1/2000 | Germa et al. | |
| 6,047,815 A | 4/2000 | Cerwin et al. | |
| 6,076,659 A | 6/2000 | Baumgartner et al. | |
| 6,096,532 A | 8/2000 | Armstrong et al. | |
| 6,098,796 A | 8/2000 | Januzeli et al. | |
| 6,105,339 A | 8/2000 | Pohle et al. | |
| 6,135,272 A | 10/2000 | Sobel et al. | |
| 6,135,385 A | 10/2000 | Martinez de Lahidalga | |
| 6,138,440 A | 10/2000 | Gemma | |
| 6,260,699 B1 | 7/2001 | Kaplan et al. | |
| 6,306,424 B1 | 10/2001 | Vyakarnam et al. | |
| 6,333,029 B1 | 12/2001 | Vyakarnam et al. | |
| 6,365,149 B2 | 4/2002 | Vyakarnam et al. | |
| 6,394,269 B1 | 5/2002 | Rudnick et al. | |
| 6,398,031 B1 | 6/2002 | Frezza | |
| 6,423,252 B1 | 7/2002 | Chun et al. | |
| 6,464,071 B2 | 10/2002 | Baumgartner | |
| 6,481,568 B1 | 11/2002 | Cerwin et al. | |
| 6,481,569 B1 | 11/2002 | Alpern | |
| 6,533,112 B2 | 3/2003 | Warnecke | |
| 6,534,084 B1 | 3/2003 | Vyakarnam et al. | |
| 6,644,469 B2 | 11/2003 | Alpern | |
| 6,648,133 B1 | 11/2003 | Blaschke et al. | |
| 6,659,994 B1 | 12/2003 | Mader et al. | |
| 6,692,738 B2 | 2/2004 | MacLaughlin et al. | |
| 6,807,737 B1 | 10/2004 | Davia | |
| 6,986,735 B2 | 1/2006 | Abraham et al. | |
| 7,056,503 B2 | 6/2006 | Rees et al. | |
| 7,078,032 B2 | 7/2006 | MacLaughlin et al. | |
| 7,112,417 B2 | 9/2006 | Vyakarnam et al. | |
| 7,121,999 B2 | 10/2006 | Abraham et al. | |
| 7,129,035 B2 | 10/2006 | Goldstein et al. | |
| 7,401,703 B2 * | 7/2008 | McMichael et al. | 206/570 |
| 2002/0156471 A1 | 10/2002 | Stern et al. | |
| 2003/0198666 A1 | 10/2003 | Abbas et al. | |
| 2004/0131956 A1 | 7/2004 | Machiguchi et al. | |
| 2004/0153125 A1 | 8/2004 | Roby | |
| 2004/0173487 A1 * | 9/2004 | Johnson et al. | 206/363 |
| 2005/0079200 A1 | 4/2005 | Rathenow et al. | |
| 2005/0167309 A1 | 8/2005 | Iwatschenko | |
| 2005/0220770 A1 | 10/2005 | Scott et al. | |
| 2005/0278012 A1 * | 12/2005 | Vonderwalde | 623/1.11 |
| 2006/0027467 A1 | 2/2006 | Ferguson | |
| 2006/0029722 A1 | 2/2006 | Larson et al. | |
| 2006/0163752 A1 | 7/2006 | Wang et al. | |
| 2006/0193884 A1 | 8/2006 | Stopek et al. | |
| 2007/0170080 A1 | 7/2007 | Stopek et al. | |

FOREIGN PATENT DOCUMENTS

| | | |
|---|---|---|
| EP | 0558085 | 9/1993 |
| EP | 0558086 | 9/1993 |
| EP | 0564274 | 10/1993 |
| EP | 0726062 | 8/1996 |
| EP | 0728445 | 8/1996 |
| EP | 1275343 | 1/2003 |
| EP | 1 312 556 | 5/2003 |
| EP | 1316291 | 6/2003 |
| GB | 1 327 865 | 8/1973 |
| JP | 10306228 | 11/1998 |
| WO | WO 98/11932 | 3/1998 |
| WO | 99/37233 | 7/1999 |
| WO | WO 01/36289 | 5/2001 |
| WO | 03/008285 | 1/2003 |
| WO | WO 03/092779 | 11/2003 |
| WO | 03/101334 | 12/2003 |
| WO | WO2006/126926 | 11/2006 |
| WO | WO2007/104107 | 9/2007 |
| WO | WO 2008/045339 | 4/2008 |

OTHER PUBLICATIONS

European Search Report, Application No. EP 07 00 1216, date of completion is May 22, 2007.
European Search Report for EP 07253902.6-1526 date of completion is Jan. 22, 2008.
International Search Report for PCT/US07/004478 date of completion is Nov. 20, 2007 (10 pages).
International Search Report for PCT/US2007/021421 date of completion is Feb. 26, 2008 (10 pages).
International Search Report for PCT/US07/021422 date of completion is May 18, 2008 (3 pages).
International Search Report for PCT/US2008/002457 date of completion is Jun. 6, 2008.
International Search Report for PCT/US2008/002458 date of completion is Jun. 10, 2008.
European Search Report for EP 11194854.3-2310 date of completion is Mar. 28, 2012 (5 pages).

* cited by examiner

MEDICAL DEVICE PACKAGE

CROSS-REFERENCE TO RELATED APPLICATIONS

This application is a continuation-in-part of co-pending U.S. patent application Ser. No. 11/340,912, filed Jan. 26, 2006, now abandoned the entire contents of which are hereby incorporated by reference herein.

BACKGROUND

1. Technical Field

The present disclosure relates generally to packaging for medical devices, and more particularly, to a package for applying a predetermined amount of at least one target agent to a medical device. The packages described herein include a container for receiving a medical device, wherein at least a portion of the medical device is prepared to receive the target agent and a port in communication with the container for allowing the sterile passage of the target agent to the prepared portions of the device.

2. Background of Related Art

Combination medical devices, i.e., medical devices coated with drugs or other bioactive agents, have become more prevalent commercially in recent years. There are many of these combination medical devices known to those skilled in the art. Many of these devices require specialized coatings to facilitate both bioactive agent elution and, more importantly, maintain or enhance the core functionality of the medical device. For example, a suture containing an antimicrobial coating must be able to facilitate the elution of the antimicrobial agent in the coating and also maintain a certain tensile strength, handling ability, knot-tying ability, and degradation rate to ensure the coated suture remains functional as a wound closure device.

In addition, significant interest has recently been placed on coupling target agents, i.e., drugs, biological molecules, etc., to the surface of a medical device to improve clinical outcomes related to improved biocompatibility, reduced implant rejection, fibrous encapsulation, localized drug delivery, and reduced infection. Much of this work has focused on using some form of chemical coupling to bridge common drugs, such as chemotherapy agents, anti-infectives, anti-inflammatories, etc., or biologics, i.e., cells, peptides, fibronectin, etc., to the surface of a medical device. It would be advantageous to have a package for receiving a medical device having a surface prepared to receive a target agent which maintained sterility while allowing for the passage of a target agent between the prepared surface of the medical device and the outside of the package.

Therefore, the present disclosure describes a package for a medical device aimed at simplifying the addition of a target agent to the prepared surface of a medical device, as well as maintaining the sterile conditions in which the addition of the target agent is conducted.

SUMMARY

Accordingly, a package for applying a predetermined amount of at least one target agent to a medical device in accordance with the present disclosure includes a container configured and dimensioned to receive a medical device, wherein at least a portion of the medical device is prepared to receive at least one target agent. The package further includes a port which is in communication with the container and allows the sterile passage of the target agent to the medical device.

In addition, the present disclosure describes methods of applying a predetermined amount of a target agent to a medical device including the steps of providing a prepared medical device in a sterile package having a port for allowing sterile passage of at least one target agent to the device, and introducing the target agent into the container through the port to interact with the prepared medical device.

BRIEF DESCRIPTION OF THE DRAWINGS

Various embodiments are described herein with reference to the drawings wherein.

DETAILED DESCRIPTION

Figure 1A:
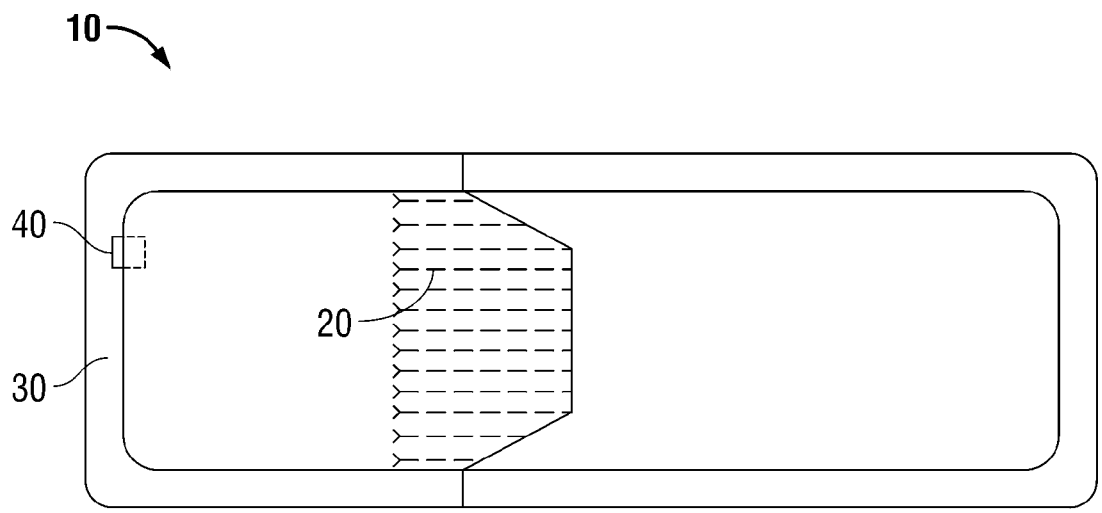
FIGS. 1A and 1B are a top and end view respectively of a package for a medical device having a surface prepared to receive a target agent.

Referring now to FIGS. 1A-2B, package 10 as described herein includes container 30 which is designed and configured to receive a medical device 20 having a surface prepared to receive at least one target agent and port 40 which is in communication with container 30 for allowing sterile passage of the target agent to medical device 20. Any medical device may be received within container 30 of package 10, including implantable, transplantable or prosthetic materials which remain in the body for at least some time.

Appropriate medical devices can be made from natural material, synthetic material or a combination of natural and synthetic material. Examples of natural materials include, for example, intact tissues as well as decellularized tissue. These tissues are often derived from a particular animal species such as human, bovine, porcine, shark and the like, and may be obtained from, for example, natural heart valves; portions of natural heart valves such as roots, walls and leaflets; pericardial tissues such as pericardial patches; connective tissues; bypass grafts; tendons; ligaments; skin patches; blood vessels; cartilage; dura matter; skin; bone; umbilical tissues; GI tract tissues; and the like. These natural tissues generally include collagen-containing material.

The devices may also be formed from tissue equivalents such as a tissue-engineered material involving a cell-repopulated matrix, which can be formed from polymers, biopolymers or from a decellularized natural tissue. Biopolymers can be naturally occurring or produced in vitro by, for example, fermentation and the like. Purified biopolymers can be appropriately formed into a substrate by techniques such as weaving, knitting, casting, molding, extrusion, cellular alignment and magnetic alignment.

Synthetic materials that can be used to form the medical devices described herein include, without limitation, a variety of biocompatible materials such as metals, such as titanium, stainless steel, and nitinol, glass, ceramics, nylons, and polymeric materials. Appropriate polymers include bioabsorbable and non-bioabsorbable materials. Some non-limiting examples include polystyrene, polycarbonate, polytetrafluoroethylene, polyethylene, polypropylene, polysaccharides, polylactides, polyglycolides, and combinations thereof.

Suitable non-limiting examples of medical devices which may be received within the packages described herein include: sutures, staples, clips, pledgets, buttresses, suture anchors, cables, wires, pacemakers, stents, catheters, inflatable devices, adhesives, sealants, meshes, sternum closures, pins, screws, tacks, rods, plates, adhesion barriers, bioelectronic devices, dental implants, surgical tools and combinations thereof.

The medical devices described herein include at least one surface, at least a portion of which is prepared to receive at least one target agent. The surface of the medical device is considered prepared to receive a target agent when it is capable of immobilizing or capturing the target agent. In some embodiments, the surface of the medical device is naturally prepared to receive the target agent. That is to say, the material used to form the medical device may inherently possess the ability to receive or immobilize a target agent thereby alleviating the need to modify the device.

In some embodiments, the surface of the medical device may be modified using any suitable method to prepare the surface for receiving the target agent. Some non-limiting examples of methods used to modify the surface of a medical device include, but are limited to, plasma-based deposition, laser-based deposition, gamma-radiation induced polymerization, chemical grafting using complimentary reactive functionality, and the like.

The surface of the medical device may be prepared anytime prior to the introduction of the target agent. In some embodiments, the surface of the medical device may be prepared prior to being sealed within the packages described herein. In some embodiments, the surface of the medical device may be prepared for receiving a target agent after being received within the package.

It is envisioned that any portion of the medical device may be modified or prepared to receive a target agent. It is further envisioned that the prepared surface may represent varying amounts of the medical device and in varying configurations, dimensions and concentrations as needed to capture or immobilize a sufficient amount of the target agent. Since only the prepared portions of the medical device can receive the target agent, the medical device is capable of receiving a specific and predetermined amount of the target agent.

In embodiments, at least a portion of a surface of the medical device is modified using coupling agents. Coupling agents are designed to interact with the surface and allow the surface of the device to receive the target agent. The coupling agents act as an intermediary between the surface of the device and the target agent and allow the prepared surface of the medical device to immobilize or capture the target agent.

The coupling agent is typically a polyvalent organic compound and in particularly useful embodiments is a divalent compound. The coupling agent may be biologically inactive, or may itself possess biological activity. The coupling agent can also comprise other electrophilic or nucleophilic functional groups (including hydroxy groups, mercapto groups, amine groups, carboxylic acids, succinimidyl groups, as well as others) that can be used to modify the surface of the medical device (e.g. for branching, for cross linking, for appending the target agents).

The coupling agent may incorporate other hydrolytically biodegradable groups such as alpha-ester (lactate, glycolate), e-caprolactone, ortho-ester, or enzymatically biodegradable groups such as amino acids. It may be a water-soluble, non-biodegradable segment such as a polyethylene glycol, polyvinyl alcohol or polyvinyl pyrrolidone.

The coupling agent may be a water-insoluble, non-biodegradable segment such as polypropylene glycol, polyetherurethane, or poly(n-alkyl ether). It may be an amorphous or semicrystalline biodegradable polymer, such as poly(d,l-lactide), poly(trimethylene carbonate), poly(dioxanone), polyanhydride poly(orthoester) poly(glycolide), poly(l-lactide) poly(e-caprolactone) and copolymers of e-caprolactone, glycolide, trimethylene carbonate, dioxanone, d,l-lactide, l-lactide and d-lactide The coupling agent may have surfactant properties, such as a Pluronic block copolymer with polyethylene glycol and polypropylene glycol blocks. It may have polar or charged moieties, including carboxylic acid groups from poly(acrylic acid) and poly(alginates), sulfonic acid groups from poly(2-acrylamido-2-methyl-propanesulfonic acid) (AMPS), hydroxy groups from poly(vinyl alcohol), polysaccharides and poly(alginates), and amino groups from poly(L-lysine), poly(2,2-dimethylaminoethyl methacrylate) and poly(amino acids).

The coupling agent may be a segment that undergoes thermoreversible gellation, such as Pluronic F127 and poly(N-isopropyl acrylamide). It may incorporate structurally-reinforcing segments, such as polyetherurethane, polyesterurethane, etc.

The coupling agent may be a polyvalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—), (—S—) or (—NR—).

The coupling agent may be a peptide, enzyme, protein, nucleotide, amino acid, polyamino acid or polypeptide.

In particularly useful embodiments, the coupling agent is at least one peptide which is capable of binding selectively to both the surface of the medical device and the target agent. The peptide may be applied, i.e., sprayed, dipped, coated, brushed, swiped, painted, injected, etc., to the surface of the medical device to allow the medical device to capture the target agent.

In still other embodiments, more than one coupling agent may be used to prepare the surface of the medical device. For example, not all coupling agents may be capable of interacting with both the medical device and the target agent. In such cases, one coupling agent may be used to bind to the surface of the medical device and another coupling agent may be used to bind to the target agent.

The at least one target agent may be selected from any bioactive and/or non-bioactive agent suitable for combination with the prepared surface of the medical device. Suitable agents include, but are not limited to, peptides, proteins, enzymes, antibodies, growth factors, cells, cell receptors, fibronectin, laminin, morphogenic factors, cell matrix proteins, genetic materials, viral vectors, nucleic acids, lymphokines, plasmids, and drugs. Some non-limiting examples of useful drug compounds include antiseptics, anesthetics, muscle relaxants, antihistamines, decongestants, antimicrobial agents, anti-viral agents, anti-fungal agents, antimalarials, amebicides, antituberculosal agents, antiretroviral agents, leprostatics, antiprotazoals, antihelmitics, antibacterial agents, steroids, hematopoietic agents, antiplatelet agents, anticoagulants, coagulants, thrombolytic agents, hemorrheologic agents, hemostatics, plasma expanders, hormones, sex hormones, uterine-active agents, bisphosphonates, antidiabetic agents, glucose-elevating agents, growth hormones, thyroid hormones, inotropic agents, antiarrhythmic agents, calcium channel blockers, vasodilators, sympatholytics, antihyperlipidemic agents, vasopressors, angiotensin antagonists, sclerosing agents, anti-impotence agents, urinary alkanizers, urinary acidifiers, anticholinergics, diuretics, bronchodilators, surfactants, antidepressants, antipsychotics, antianxiety agents, sedatives, hypnotics, barbiturates, antiemetic agents, analgesics, stimulants, anticonvulsants, antiparkinson agents, proton pump inhibitors, $H_2$-antagonists, antispasmodics, laxatives, antidiarrheals, antiflatulents, digestive enzymes, gallstone solubilizing agents, antihypertensive agents, cholesterol-lowering agents, radiopaque agents, immune globulins, antitoxins, antivenins, immunologic agents, anti-inflammatory agents, antineoplastic agents, alkylating agents, antimetabolites, antimitotic agents, radiopharmaceuticals, vitamins, herbs, trace elements, amino acids, chelating agents, immunomodulatory agents, immunosuppressive agents, diluents, radioactive agents, immuneglobulis, preservatives; colorants; dyes; ultraviolet absorbers; ultraviolet stabilizers; photochromic agents; anti-adhesives; polysaccharides; growth factor antagonists; anti-colonization agents; diagnostic agents; imaging agents; and combinations thereof.

In some embodiments, the target agent includes any agent previously described herein combined with a polymeric material. The agent can be combined with a polymer in any suitable manner, such as, e.g., by physically admixing, embedding or dispersing the agent in the polymer matrix. In one embodiment, the agent is attached directly to a polymer, chemically linked to a polymer through a linker or spacer molecule, directly or indirectly chemically linked to a chemical group attached to the backbone of a polymer and/or electrostatically attached to the polymer or the polymer backbone. It is envisioned that the agents can be attached to repeating units of a polymer by covalent bonds, providing for sustained release of the active agent or it may merely reside in the unoccupied spaces present in a polymer. In another embodiment, the agent may form a salt with a polymer or a polymer backbone. In one embodiment, the agent is located in the unoccupied spaces present in a polymer and is present as a homogeneous functional group or it may be incorporated into a salt, micelle, liposome, or heterogeneous aggregate.

Figure 1B:
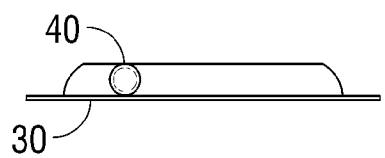

The packages described herein are useful in applying a predetermined amount of a target agent to a medical device and include at least one container for receiving the medical device. The container may take the shape of any conventional enclosure for storing medical devices manufactured from any suitable material known to those skilled in the art. The container may be sealable, non-sealable, breathable, non-breathable, peelable and combinations thereof. Some examples of useful enclosures include, but are not limited too, pouches, paper retainers, plastic retainers, envelopes, foil-packs, and the like. In one embodiment, the container is formed by heat sealing two panels of aluminum foil coated on the interior surfaces thereof with a heat sealable polymeric composition. The foil-pack is bonded around the periphery of the container. Other means for sealing the container may be employed as is well known to those skilled in the art. In other embodiments, at least one layer of aluminum foil or polymeric material may be positioned around the outer periphery of a plastic container to form a sealable package, as shown in FIGS. 1A and 1B. In still other embodiments, more than one container may be formed within the package which contains a medical device (See FIGS. 2A and 2B).

The container may be manufactured from any material known to those skilled in the art which is suitable for receiving or storing a medical device. Some examples of suitable materials include, but are not limited to, polycarbonate, high-density polyethylene, polyethylene, polypropylene, thermoplastic elastomers, thermosets, thermoplastic resins, poly(ethylene terephthalate), polytetrafluoroethylene, ε-caprolactone, glycolide, l-lactide, d,l-lactide, d-lactide, meso-lactide, trimethylene carbonate, 4,4-dimethyl-1,3-dioxan-2-one, p-dioxanone, dioxepanone, δ-valerolactone, β-butyrolactone, ε-decalactone, 2,5-diketomorpholine, pivalolactone, α,α-diethylpropiolactone, 6,8-dioxabicyclooctan-7-one, ethylene carbonate, ethylene oxalate, 3-methyl-1,4-dioxane-2,5-dione, 3,3-dimethyl-1,4-dioxane-2,5-dione, polyolefins, polysiloxanes, polyalkylene glycols, polyacrylates, aminoalkyl acrylates, polyvinylalcohols, polyvinylpyrrolidones, polyoxyethylenes, polyacrylamides, poly(2-hydroxy-ethylmethacrylate), polymethacrylamide, dextran, alginic acid, sodium alginate, polysaccharides, gelatin and copolymers, homopolymers, and block copolymers thereof.

In addition to the container and the medical device, the packages described herein include a port. The port is designed to permit the passage of at least one target agent between the outside of the package or container and the prepared surface of the medical device contained inside the container. It is envisioned that the port may be sealable, non-sealable, stationary, movable, peelable and combinations thereof.

Figure 2A:
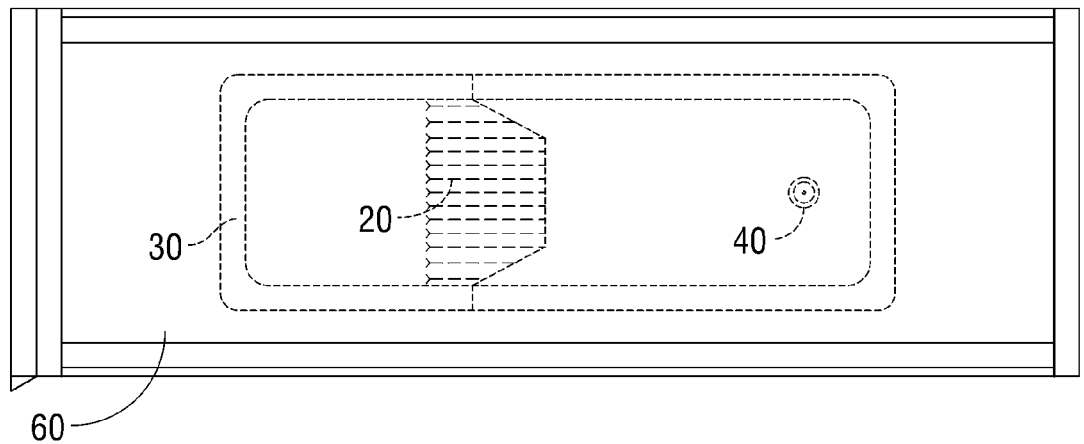
FIGS. 2A and 2B are a top and side view of a port, positioned within and through an outer breathable pouch and a container for receiving a medical device having a surface prepared to receive a target agent, for permitting the passage of a target agent between the outside of the package and the prepared surface of the medical device positioned within the container.
Figure 2B:
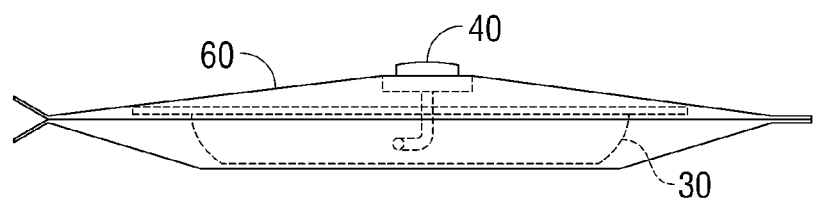

As shown in FIGS. 1A and 1B, port 40 may be positioned along any side, edge or corner of container 30. In embodiments wherein package 10 includes more than one container 30, port 40 may be positioned alone any side, edge or corner of any of the cavities included in package 10. In embodiments. port 40 may be positioned.on the outer or inner surface of outer. breathable package 60, as shown in FIGS. 2A-2B wherein port 40 is adjacent the outer periphery of sealable pouch 30. It is envisioned that port 40 may be located anywhere adjacent a periphery of scalable pouch 30, including for example. the inner or outer surfaces of sealable pouch 30. In one embodiment. port 40 may he positioned within and through the surface of sealable pouch 30 or outer breathable package 60. In the embodiment illustrated in FIGS. 2A-2B, port 40 is sealed within the surface of sealable pouch 30 or outer breathable retainer 60 and passes through into the selected retainer or pouch. In another embodiment, port 40 may be positioned only on the surface of sealable pouch 30 or outer breathable package 60. It is further envisioned that port 40 may be adhered to a surface with an adhesive that allows port 40 to be easily peeled away from the surface and adhered to another surface of the pouch, thereby allowing port 40 to be repositioned to another surface within package 10.

Additionally in FIGS. 1A and 1B, port 40 is shown as an injectable-hub which is designed to remain sealed by self-sealing action to ensure no fluid medium can escape and also so no pathogens can breach the container. Port 40 can be composed of a traditional rubber or thermoplastic material known to be used in sealing sterile vials, intravenous bags, catheters, drug ampules or blood bags. Alternatively, port 40 may be composed of hydrophobic, hydrophilic or a combination of hydrophobic and hydrophilic materials. Suitable ports can be made of any size, shape or dimension.

In one embodiment, port 40 may be a hub designed in such a way that only a particular syringe can mate with port 40 thereby creating a lock and key type of hub to promote only specific use of port 40. This type of hub provides more safety to the user of port 40 because the hub does not necessarily require the use of a needle. In addition, the lock and key type of hub may be used by patients and medical staff for only certain medications and dosages of those medications, thereby reducing the likelihood of administering the wrong agent or the wrong dosage of the intended agent.

As shown in FIGS. 2A and 2B, package 10 includes container 30 which is positioned within a second container 60 wherein port 40 passes through second container 60 and penetrates into container 30. In embodiments, container 60 is a breathable pouch. By penetrating into container 30, port 40 can direct the target agent into any specific area within container 30 including particular areas of the medical device 20 or any additional cavities included within package 10. In addition, the shunt can be positioned to further penetrate the medical device 20 or any additional cavities included within package 10 to increase the wetting rate of medical device 20 and/or limit the target agent to only certain areas of the medical device 20.

In still other embodiments, port 40 may be incorporated with an additional separate container which may be filled with the target agent. In some embodiments, the separate container is a frangible container which can be filled with at least one target agent either prior to or following the production of the package. In this embodiment, the surgeon or other medical staff may apply pressure to the frangible container thereby forcing frangible container to open and release the target agent into the port which will permit the passage of the target agent into the container and onto the prepared surface of the medical device. The frangible container may be manufactured from any material known to those skilled in the art. One known example includes glass materials. In embodiments where the frangible container is made from glass or other materials not meant to be introduced to the patient, a filter may be connected to the port, between the frangible container and the port, to keep these materials from entering the port following the opening of the frangible container.

Figure 3:
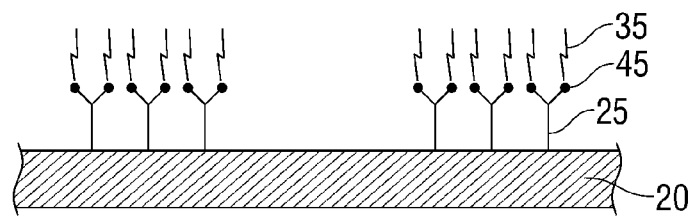
FIG. 3 is a side view of a medical device receiving a target agent on the portions of the medical device surface that are prepared to receive the target agent.

Turning now to FIG. 3, medical device 20 is shown having a prepared surface 25 for receiving at least one target agent 35. Target agent 35 is shown immobilized on the portions of medical device 20 which have been prepared 25. In some embodiments, coupling agent 45 may be used as an intermediary between prepared surface 25 of medical device 20 and target agent 35. As shown, target agent 35 is immobilized on only the prepared portions of the medical device thereby allowing a predetermined amount of target agent to be applied to the medical device.

In embodiments, the coupling agent may be applied to the medical device to form a prepared surface. In embodiments, the coupling agent may be combined with the target agent prior to being introduced to the prepared surface of the medical device.

It is well understood that various modifications may be made to the embodiments disclosed herein. Therefore, the above description should not be construed as limiting, but merely as exemplifications of particularly useful embodiments. Those skilled in the art will envision other modifications within the scope and spirit of the claims appended hereto.

We claim:

1. A kit, comprising:
 at least one target agent;
 a breathable pouch;
 a sealed container disposed within the breathable pouch;
 a medical device disposed in the sealed container, wherein at least a portion of the medical device is prepared to receive the at least one target agent on the at least a portion of the medical device; and
 a port disposed in an outer surface of the breathable pouch in communication with the sealed container for allowing sterile passage of the at least one target agent from outside the breathable pouch to the at least a portion of the medical device disposed in the sealed container, wherein the port passes through the breathable pouch and penetrates into the sealed container to direct the at least one target agent into one or more areas defined within the sealed container.

2. The kit of claim 1, wherein the at least a portion of the medical device is prepared by a method selected from the group consisting of plasma-deposition, laser-based deposition, gamma-radiation induced polymerization, and chemical grafting using complimentary reactive functionality.

3. The kit of claim 1, wherein the at least a portion of the medical device is prepared by the addition of at least one coupling agent.

4. The kit of claim 1 wherein the at least one target agent is selected from the group consisting of peptides, proteins, enzymes, antibodies, growth factors, cells, cell receptors, fibronectin, laminin, morphogenic factors, cell matrix proteins, genetic materials, viral vectors, nucleic acids, lymphokines, plasmids, drugs and combinations thereof.

5. The kit of claim 1 wherein the at least one target agent is a drug.

6. The kit of claim 5 wherein the drug is selected from the group consisting of antiseptics, anesthetics, muscle relaxants, antihistamines, decongestants, antimicrobial agents, anti-viral agents, anti-fungal agents, antimalarials, amebicides, antituberculosal agents, antiretroviral agents, leprostatics, antiprotazoals, antihelmitics, antibacterial agents, steroids, hematopoietic agents, antiplatelet agents, anticoagulants, coagulants, thrombolytic agents, hemorrheologic agents, hemostatics, plasma expanders, hormones, sex hormones, uterine-active agents, bisphosphonates, antidiabetic agents, glucose-elevating agents, growth hormones, thyroid hormones, inotropic agents, antiarrhythmic agents, calcium channel blockers, vasodilators, sympatholytics, antihyperlipidemic agents, vasopressors, angiotensin antagonists, sclerosing agents, anti-impotence agents, urinary alkanizers, urinary acidifiers, anticholinergics, diuretics, bronchodilators, surfactants, antidepressants, antipsychotics, antianxiety agents, sedatives, hypnotics, barbiturates, antiemetic agents, analgesics, stimulants, anticonvulsants, antiparkinson agents, proton pump inhibitors, $H_2$-antagonists, antispasmodics, laxatives, antidiarrheals, antiflatulents, digestive enzymes, gallstone solubilizing agents, antihypertensive agents, cholesterol-lowering agents, radiopaque agents, immune globulins, monoclonal antibodies, antibodies, antitoxins, antivenins, immunologic agents, anti-inflammatory agents, antineoplastic agents, alkylating agents, antimetabolites, antimitotic agents, radiopharmaceuticals, vitamins, herbs, trace elements, amino acids, enzymes, chelating agents, immunomodulatory agents, immunosuppressive agents and combinations thereof.

7. The kit of claim 1, wherein the breathable pouch is configured to maintain sterility of the sealed container disposed within the breathable pouch.

8. A kit, comprising:
 at least one target agent;
 a breathable pouch;
 a sealed container disposed within the breathable pouch;
 a medical device disposed in the sealed container; and
 a port including a sealed port disposed at an outer surface of the breathable pouch, the port further including a conduit communicatively coupling the sealed port and the sealed container for allowing sterile passage of the at least one target agent from outside the breathable pouch to the at least a portion of the medical device disposed in the sealed container, wherein the conduit passes through the breathable pouch and penetrates into the sealed container to direct the at least one target agent into one or more areas defined within the sealed container.

9. A sterile package for applying a predetermined amount of at least one target agent to a medical device, comprising:
a breathable pouch;
a sealed container disposed within the breathable pouch;
a port including a sealed port disposed at an outer surface of the breathable pouch, the port further including a conduit communicatively coupling the sealed port and the sealed container for allowing sterile passage of the at least one target agent from outside the breathable pouch to at least a portion of the medical device disposed in the sealed container, wherein the conduit passes through the breathable pouch and penetrates into the sealed container to direct the at least one target agent into one or more areas defined within the sealed container.

10. The kit of claim 1, wherein the port includes a frangible container for retaining the at least one target agent.

11. The kit of claim 10, wherein the frangible container is formed of glass.

12. The kit of claim 1, wherein the port includes a filter.

* * * * *